US00PP22280P2

(12) United States Plant Patent
Richards

(10) Patent No.: US PP22,280 P2
(45) Date of Patent: Nov. 29, 2011

(54) ***IBERIS* PLANT NAMED 'MASTERPIECE'**

(50) Latin Name: ***Iberis* hybrid**
Varietal Denomination: Masterpiece

(76) Inventor: Rodney W. Richards, Hereford (GB)

( * ) Notice: Subject to any disclaimer, the term of this patent is extended or adjusted under 35 U.S.C. 154(b) by 0 days.

(21) Appl. No.: 12/804,237

(22) Filed: Jul. 16, 2010

(51) Int. Cl.
*A01H 5/00* (2006.01)

(52) U.S. Cl. ..... Plt./263.1
(58) Field of Classification Search ..... Plt./263.1
See application file for complete search history.

*Primary Examiner* — June Hwu
*Assistant Examiner* — Louanne Krawczewicz Myers
(74) *Attorney, Agent, or Firm* — Penny J. Aguirre

(57) ABSTRACT

A new cultivar of *Iberis,* 'Masterpiece', characterized by its strong, densely branched, and stocky vegetation, its very long flowering period, blooming from at least April to August in the U.K., its large white inflorescences that fade to pale pink, its cold hardiness at least to 6° F., and its mildew resistance.

2 Drawing Sheets

Botanical classification: *Iberis* hybrid.
Variety denomination: 'Masterpiece'.

BACKGROUND OF THE INVENTION

The present invention relates to a new and distinct cultivar of *Iberis* plant, botanically of hybrid origin and known as *Iberis* 'Masterpiece' and will be referred to hereinafter by its cultivar name, 'Masterpiece'. The new cultivar represents a new cultivar of *Iberis,* an herbaceous perennial grown for landscape use.

A descendent plant of 'Masterpiece' was discovered by the Inventor in Headley Down, Hampshire, UK in 2004 in a trial bed containing the Inventor's collection of both unnamed and named varieties of *Iberis*. Repeated selections were made in a trial bed in Hereford, Herefordshire, U.K. between 2004 and 2007 and 'Masterpiece' was selected as a single unique plant in 2007. The parentage is not known, however it is likely that 'Masterpiece' is a hybrid between *Iberis sempervirens* and *Iberis gibraltarica* based on the characteristics of 'Masterpiece' and their proximity to the location where 'Masterpiece' was discovered.

Asexual reproduction of the new cultivar was first accomplished by the Inventor via stem cuttings in 2007 in, Hereford, Herefordshire, U.K. The characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'Masterpiece' as unique from all other varieties of *Iberis* known to the Inventor.

1. 'Masterpiece' exhibits a strong, densely branched, and stocky vegetation.
2. 'Masterpiece' exhibits a very long flowering period, blooming from at least April to August in the U.K.
3. 'Masterpiece' exhibits large white inflorescences that fade to pale pink, typically at least 5 cm (2 inches) in diameter.
4. 'Masterpiece' is cold hardy at least to 6° F.
5. 'Masterpiece' has been observed to be mildew resistant.

'Masterpiece' can be compared to the probable parent plants, *Iberis sempervirens* and *Iberis gibraltarica*. *Iberis sempervirens* differs from 'Masterpiece' in having smaller flowers and a less densely branched plant habit. *Iberis gibraltarica* differs from 'Masterpiece' in being less hardy in the U.K. and in having flowers that are violet in color. 'Masterpiece' can also be compared to 'Golden Candy' (not patented), which has smaller flowers and yellow-green leaves, 'Snowflake' (not patented), which is shorter in height and has a shorter bloom period, blooming from spring to early summer, and 'Purity' (not patented), which is very short in height and blooms in early spring and may rebloom in fall, but lacks a continuous blooming habit as observed for 'Masterpiece'.

BRIEF DESCRIPTION OF THE DRAWING

The accompanying colored photographs illustrate the overall appearance and distinct characteristics of the new *Iberis*.

The photograph in FIG. 1 was taken of a plant about 8 months in age as grown outdoors in a one-gallon container in Watsville, Calif. and provides a view of the plant habit of 'Masterpiece' in bloom.

Figure 1:
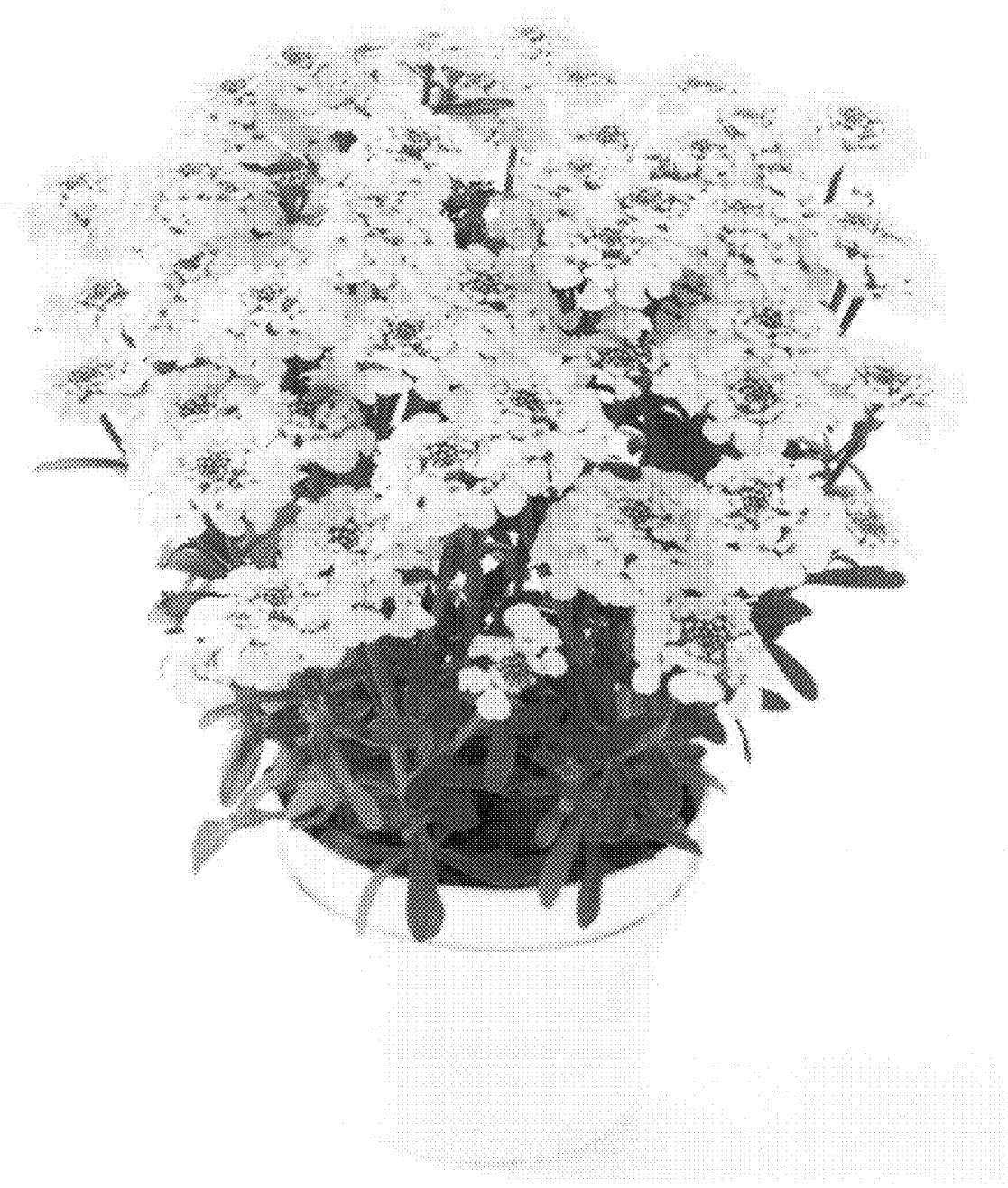
Figure 2:
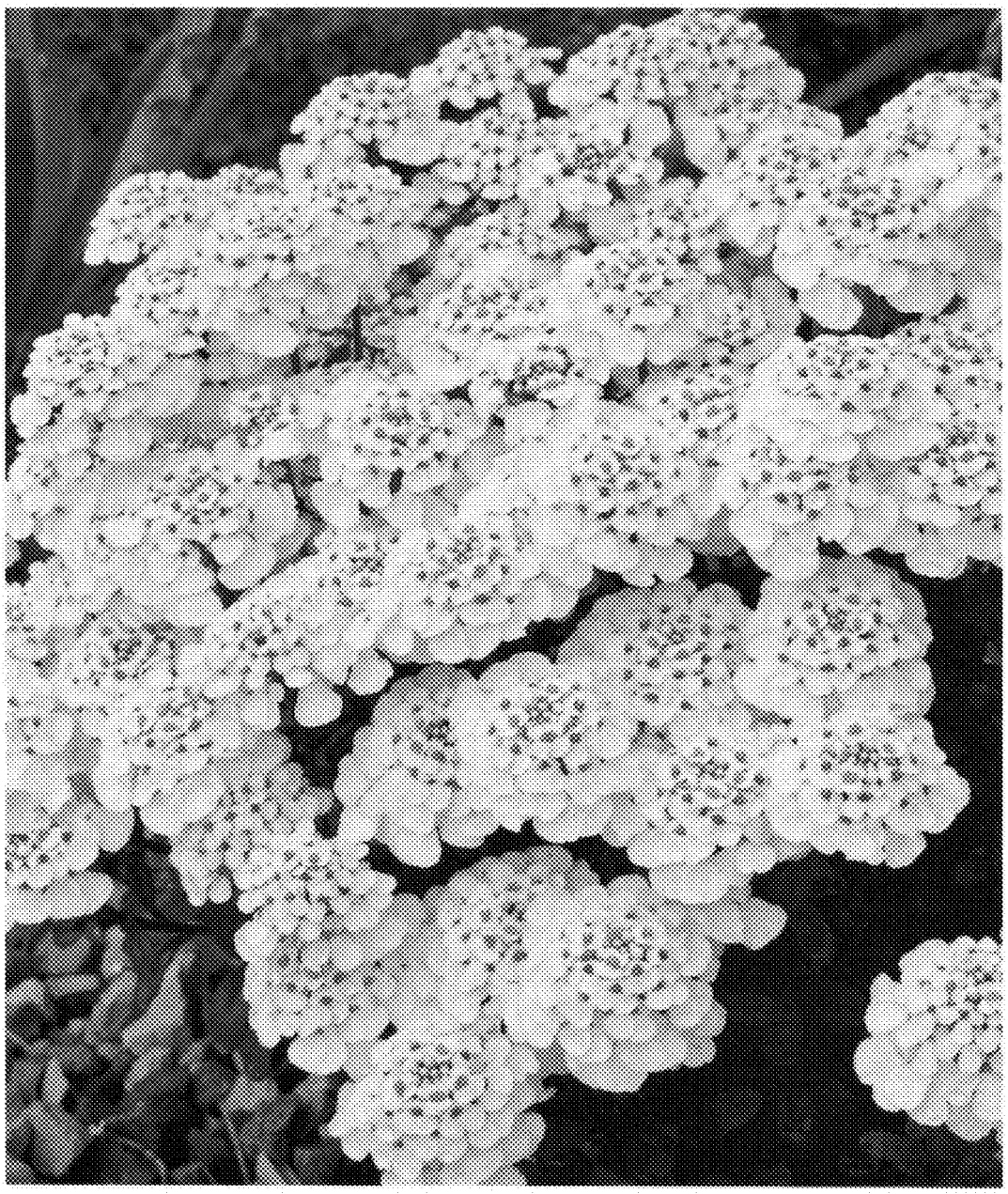

The photograph in FIG. 2 was taken of a 5 year-old plant as grown in a garden in Hereford, Herefordshire, U.K. and provides a close-up view of the flowers of 'Masterpiece'.

The color values cited in the detailed botanical description accurately describe the colors of the new *Iberis*.

DETAILED BOTANICAL DESCRIPTION

The following is a detailed description of a plant about 8 months in age of the new cultivar as grown outdoors in a 6 cm-container in Watsonville, Calif. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Very long flowering period, blooming from at least April to August in the U.K.

*Plant habit.*—Herbaceous perennial, upright mound, dense, and strong.

*Height and spread.*—Matures to about 30 cm in height and about 27 cm in width.

*Hardiness.*—At least to 6° F. in the U.K.

*Diseases and pests.*—Has shown resistance to powdery mildew in the U.K.

*Root description.*—Fibrous.

Growth and propagation:

*Propagation.*—Stem cuttings.

*Growth rate.*—Moderate.

Stem description:

*Stem strength.*—Strong and held upright.

*Shape.*—Round with ridges.

*Stem color.*—Between 143A to 143B.

*Stem size.*—Average of 2.5 mm in diameter and 25 cm in length (including peduncle).

*Stem surface.*—Ridged and moderately pubescent.

*Branching habit.*—Numerous branches emerge from woody (old wood) stems, 1 to 2 sublateral branches per lateral branch, 61 branches in a 6 cm container.

Foliage description:

*Leaf division.*—Simple.

*Leaf shape.*—Spatulate.

*Leaf base.*—Blunt, clasping to stem.

*Leaf apex.*—Obtuse to slightly acute.

*Leaf margin.*—Entire, sparsely pubescent.

*Leaf venation.*—Not discernable.

*Leaf attachment.*—Sessile.

*Leaf arrangement.*—Whorled.

*Leaf surface.*—Glandular on upper and lower surfaces.

*Leaf color.*—Newly emerged and mature upper surface; 137A, newly emerged and mature lower surface; 137C.

*Leaf aspect.*—Recurved.

*Leaf size.*—An average of 3.8 cm in length and 1.1 cm in width.

*Foliage fragrance.*—None.

Flower description:

General description:

*Type.*—Rounded raceme.

*Lastingness of inflorescence on the plant.*—About 3 weeks.

*Fragrance.*—Pungent.

*Quantity of inflorescences.*—One per terminal and one per lateral branch.

*Infloresences size.*—An average of 5 cm in diameter and 3.4 cm in depth for terminal corymbs, an average of 3.6 cm in diameter and 3 cm in depth for lateral corymbs.

*Flower type.*—Polysymetric with 2 smaller adaxial petals and 2 larger abaxial petals.

*Flower size.*—About 1.2 cm in diameter and 7 mm in depth.

*Flower number.*—Average of 27 on terminal corymbs and 15 on lateral corymbs.

*Flower buds.*—About 3 mm in height and diameter, globose in shape, color NN155D with sepal portion 144A.

*Peduncle.*—Primary an average of 4.5 cm in length and 3 mm in diameter with laterals an average of 2 cm in length and 2 mm in width, 143A in color, surface is moderately pubescent.

*Pedicels.*—An average of 1.3 cm in length and 1 mm in diameter, 143A in color, surface is moderately pubescent.

*Petals.*—4, 2 adaxial and 2 abaxial, adaxial; limb strongly reflexed, limb is orbicular in shape, glabrous surface, rounded apex, margins entire, limb is about 4 mm in width and length, claw is about 2 mm in length and 0.5 mm in width with truncate base, NN155D in color on upper and lower surfaces, abaxial; limb held outward, rotund in shape, glabrous surface, rounded apex, margins entire, limb is about 6 mm in width and 7 mm in length, claw is about 3 mm in length and 1 mm in width with truncate base, NN155D in color on upper and lowers surfaces.

*Calyx.*—Open campanulate in form, 4 mm in height and 6 mm in width.

*Sepals.*—4, un-fused, oblong in shape, an average of 4 mm in height and 2 mm in width, acute apex, truncate base, glabrous on outer and inner surfaces, color of outer and inner surface; margins N155D, centers 143C.

Reproductive organs:

*Gynoecium.*—Pistil; 1, style; 155D in color, crystalline in appearance, about 6 mm in length and <1 mm in width, 144A in color, stigma; minute, 161A in color, ovary; superior, rounded oblong in shape with 2 pointed apex and style running through it, 3.5 mm in length and width, 144A in color.

*Androcoecium.*—Stamens; 4, un-fused, filament; N155D in color and suffused with N79C, about 5 mm in length, crystalline in appearance, anther; 177B in color, dorsifixed, about 1.5 mm in length and 1 mm in width, pollen; moderate in quantity and 161A in color.

*Fruit and seed.*—Not observed under the conditions tested.

It is claimed:

1. A new and distinct cultivar of *Iberis* plant named 'Masterpiece' as herein illustrated and described.

* * * * *